(12) United States Patent
Schmid

(10) Patent No.: US 7,840,273 B2
(45) Date of Patent: Nov. 23, 2010

(54) DEVICE FOR ELECTRICALLY STIMULATING BIOLOGICAL MATERIAL

(75) Inventor: Erich Schmid, Tuebingen (DE)

(73) Assignee: Universitaet Tuebingen, Tuebingen (DE)

( * ) Notice: Subject to any disclaimer, the term of this patent is extended or adjusted under 35 U.S.C. 154(b) by 430 days.

(21) Appl. No.: 11/911,472

(22) PCT Filed: Apr. 12, 2006

(86) PCT No.: PCT/EP2006/003365

§ 371 (c)(1),
(2), (4) Date: May 28, 2008

(87) PCT Pub. No.: WO2006/108630

PCT Pub. Date: Oct. 19, 2006

(65) Prior Publication Data

US 2008/0288021 A1    Nov. 20, 2008

(30) Foreign Application Priority Data

Apr. 12, 2005   (DE) ...................... 10 2005 017 740

(51) Int. Cl.
*A61N 1/00* (2006.01)
(52) U.S. Cl. ...................................... 607/53
(58) Field of Classification Search .................. 607/53, 607/54; 623/6.63
See application file for complete search history.

(56) References Cited

U.S. PATENT DOCUMENTS

| 4,628,933 | A | 12/1986 | Michelson |
| 6,400,989 | B1 | 6/2002 | Eckmiller |
| 6,530,954 | B1 | 3/2003 | Eckmiller |
| 7,257,446 | B2 | 8/2007 | Greenberg et al. |

(Continued)

FOREIGN PATENT DOCUMENTS

DE    197 05 987 C2    5/1998

(Continued)

OTHER PUBLICATIONS

Joseph F. Rizzo III et al. "Perceptual Efficacy of Electrical Stimulation of Human Retina with a microelectric Array during Short-Term Surgical Trials", Investigative Ophthalmology & Visual Science, Dec. 2003, vol. 44, No. 12, pp. 5362-5369.

(Continued)

*Primary Examiner*—George Manuel
(74) *Attorney, Agent, or Firm*—Crowell & Moring LLP

(57) ABSTRACT

A device for electrically stimulating biological material with an implantable electrode array placed in active contact with the biological material. The array has a two-dimensional arrangement of individual electrodes (Eij) that produce a stimulation field (S1, S2,) for the biological material when a stimulation signal is provided, and an apparatus for providing stimulation signals. Alternating field stimulation signals (Vij) are provided to the individual electrodes (Eij) and the electrode array has at least two tripolar or higher multipolar multipole elementary cells (T1, T2,; Q1, Q2,) from three or more adjacent individual electrodes each, and the stimulation fields (S1, S2,) produced by every multipole elementary cell for the biological material has a rotational component, and at least one of the individual electrodes pertains to at least two multipole elementary cells. Method of use, e.g. with retina implants are also provided.

23 Claims, 4 Drawing Sheets

U.S. PATENT DOCUMENTS

| | | |
|---|---|---|
| 7,574,263 B2 * | 8/2009 | Greenberg et al. ............ 607/54 |
| 2002/0038134 A1 | 3/2002 | Greenberg et al. |
| 2002/0091422 A1 | 7/2002 | Greenberg et al. |
| 2004/0267344 A1 | 12/2004 | Stett et al. |
| 2005/0021107 A1 | 1/2005 | Firlik et al. |
| 2006/0184245 A1 | 8/2006 | Graf et al. |

FOREIGN PATENT DOCUMENTS

| | | |
|---|---|---|
| DE | 101 51 650 A1 | 5/2003 |
| DE | 103 29 615 A1 | 3/2005 |

OTHER PUBLICATIONS

Dr. Alfred Stett et al. "Subretinale Sehprothesen fuer Blinde" Bulletin SEV/VSE, Mar. 1999, pp. 11-17.

Joseph F. Rizzo III et al. "Methods and Perceptual Thresholds for Short-Term Electrical Stimulation of the Human Retina with Microelectric Arrays", Investigative Ophthalmology & Visual Science, Dec. 2003, vol. 44, No. 12, pp. 5355-5361.

International Search Report dated Jul. 19, 2006 with English translation (Six (6) Pages).

German Office Action dated Nov. 4, 2005 (Three (3) Pages).

Form PCT/ISA/237 with English translation of relevant portion (Eight (8) Pages).

* cited by examiner t=0 t=τ/6 t=2τ/6 t=3τ/6 t=4τ/6 t=5τ/6 t=0 t=τ/8 t=2τ/8 t=3τ/8 t=4τ/8 t=5τ/8 t=6τ/8 t=7τ/8

DEVICE FOR ELECTRICALLY STIMULATING BIOLOGICAL MATERIAL

FIELD OF THE INVENTION

The invention relates to a device for electrically stimulating biological material that can be electrically stimulated, in particular the retinal material.

BACKGROUND AND SUMMARY OF THE INVENTION

There exist devices of this type in various designs. One applicable type, which is currently the object of intensive development, is the so-called implantable retina prosthetic or retina implant. They usually include an electrode array, which can be implanted in the subretina or epiretina in active contact with the retinal tissue that can be electrically stimulated. Said electrode array is supposed to compensate at least to a certain degree for the degeneration of the retinal photoreceptors that leads to blindness. That is, the electrode array is supposed to replace the function of the retinal photoreceptors with a space-resolved electric stimulation of the neural cells in the retina.

The most common of these devices is the unipolar stimulating electrode array, also called the monopolar type, where an electrode array chip carries a two dimensional arrangement of individual stimulation electrodes on a front side, which in the implanted state faces the retinal tissue that can be stimulated. These stimulation electrodes are assigned a planar counter-electrode at a relatively far distance in front of the front side or on the back side of the chip—that is, at a distance that is very much larger than the distance between the adjacent stimulation electrodes. A suitable medium can be used to apply a stimulation signal to the stimulation electrodes. This stimulation signal is usually a pulsed voltage signal, by means of which said stimulation electrodes generate a stimulation field—usually in the form of electric currents between the stimulation electrodes, on the one hand, and the counter-electrode, on the other hand—in the adjacent retinal tissue that can be stimulated. In a passive array type the energy required for stimulation is taken solely from the incident visible light by means of, for example, a photodiode layer sequence in the array chip. In order to achieve higher stimulation currents with simultaneously optimal spatial resolution and consequently with miniature stimulation electrodes, additional energy is fed, for example, into an active array type by means of pulsed infrared radiation. For this and other details about unipolar electrode arrays reference is made to the pertinent literature. See also the published patent applications (Offenlegungsschrift) DE 101 51 650 A1 and DE 103 29 615 A1 as well as the patent DE 197 05 987 C2.

In order to achieve simultaneously a satisfactory spatial resolution and response sensitivity for such retina implants, in principle an electrode array with a very dense arrangement of single micro-electrodes, which are capable of delivering a high stimulation field—that is, stimulation currents that exceed an excitation threshold value of the retinal cells—, and of acquiring a large stimulation volume, in which the stimulation field exceeds the excitation threshold value of the retinal cells, is desirable. On the other hand, stimulation fields that are too high locally and that could lead to tissue damage must be avoided.

At this point the conventional unipolar electrode arrays appear to reach their limit. The fact that only transient currents are observed when a voltage is applied to the stimulation electrodes is ascribed to the formation of a Helmholtz double layer at the interface between the electrode array and the tissue of the retina, even though the active mechanism of this phenomenon has not been explained in detail yet. In order to achieve higher transient currents the literature suggests a porous design of the stimulation electrodes with suitably elevated electrode surfaces. See, for example, the journal article by A. Stett and H. Hämmerle, "Subretinal Prosthetics for the Blind", *Bulletin SEV/VSE* March 1999, p. 11. Such research is not very likely to support the observation of the electrode array—retinal tissue—interface as a purely electric capacitor. Rather it is more likely to point to the "battery effect" on account of the electrolytic properties of the tissue. If the stimulation electrodes are packed more densely and the electric current density is higher, a collective current effect can also be expected with unipolar electrode arrays. Such an effect can lead to undesired high voltage drops and to the dependency of the voltage to be applied for stimulation on the number of stimulation electrodes that are active—that is, whether the visual environment is bright or dark.

As an alternative to the monopolar electrode array, one has also already experimented with bipolar electrode arrays, where front-sided counter-electrodes have been assigned individually to front-sided stimulation electrodes. Since the propagation of the electric current is locally restricted in the tissue of the retina, such a bipolar arrangement has been attributed the ability to generate, as compared to the monopolar type, more intensive voltage drops in the area between the electrodes (as stated by A. Stett and H. Hämmerle in the above-cited journal article). The journal article by J. F. Rizzo III et al., "Methods and perceptual thresholds for short-term electrical stimulation of the human retina with micro-electrode arrays", *Investigative Opthalmology & Visual Science*, December 2003, volume 44, no. 12, p. 5355, discloses not only monopolar electrode arrays, but also a bipolar electrode array with circular front-sided stimulation electrodes, which are separated from a front-sided contiguous counter-electrode by means of an annular gap.

The invention is based on the technical problem of providing a device of the type that is described in the introduction and with which even in the event of a high electrode integration density a biological material that can be stimulated can be electrically stimulated with comparatively high stimulation efficiency by using an implantable electrode array.

The invention solves this problem by providing a device with the features of claim 1. This device is designed in such a manner that the alternating field stimulation signals are applied to the individual electrodes of the electrode array, which can be implanted in active contact with the biological material that can be electrically stimulated; that the electrode array forms at least two tripolar or higher multipolar multipole elementary cells from three or more adjacent single electrodes. The stimulation field, which is produced from each multipole elementary cell for the biological material and which may have the form of electric stimulation currents, exhibits a rotation component; and at least one of the individual electrodes belongs to at least two multipole elementary cells. Hence, it is possible to produce a total stimulation field from the individual multipole fields of the elementary cells with a rotating field component. The field components of every two adjacent multipole elementary cells may rotate, for example, simultaneously and counter-clockwise.

Owing to the "lighthouse effect" of the rotation, the rotation of the stimulation field makes possible a significant increase in the probability that a stimulable cell in the adjacent biological material is "hit" by a local stimulation vector that exceeds the cell's excitation threshold value and is, thus, actually stimulated. At the same time it must be taken into consideration that especially in retinal application the stimulable cells in the biological material are generally arranged in a relatively random manner in a network; and in addition, their excitation threshold value is usually direction-dependent. Thus, in the case of cylindrical/rod-shaped axons and dentrites of the retina it is observed that they are stimulated more easily parallel to their cylindrical direction (that is, with a lower excitation threshold value) than in the direction orthogonal thereto. Rotating the stimulation field enhances the probability that a stimulable cell will be "hit" by an adequately high stimulation field vector even in a worse stimulation direction or at least will still be hit by a stimulation field vector in a good stimulation direction with a then lower excitation threshold value. In both cases the cell is then stimulated, whereas in the case of a non-rotating stimulation field the cell would not be hit with an adequately large excitation field vector and would, therefore, not be simulated.

In other words, the inventive rotation of the stimulation field enhances the stimulation efficiency and increases the stimulation volume, i.e., the volume of the biological material that can be stimulated by the stimulation field, a feature that is very important especially for very tight electrode spacing. Depending on the application, other field components—for example, a time-pulsing component and/or an oscillation component, i.e., a component that oscillates in two opposing directions—can be superimposed on the rotation component.

In an advantageous further development of the invention, the three or more adjacent, corresponding multipole elementary cells (that is, single electrodes that are coupled as a tripole, quadrupole, etc.), are actuated with the alternating field stimulation signal in such a manner that the stimulation field that said electrodes jointly produce in the biological material exhibits a field component that rotates about a multipole axis. This multipole actuation of the individual electrodes is an especially simple to realize and effective possibility for producing a stimulation field with a rotation component. Therefore, in another design of the invention a stimulation field can be produced with a field component, which rotates at a constant angular velocity, by applying alternating voltage signals, which are suitably phase shifted with respect to each other, to the individual electrodes of the multipole. At the same time an oscillation component may be generated. By coupling the individual electrodes to one or more multipoles a correspondingly multipolar electrode array is formed, in which each individual electrode of the multipole(s) acts as both a stimulation electrode and as a counter-electrode in the conventional sense. That is, the individual electrodes may all be located on the front side of the electrode array that in the implanted state faces the biological material; and the at least tripolar electrode array forms a higher polar expansion of the aforementioned monopolar and bipolar electrode array.

In a further development of the invention, the individual electrodes of the electrode array form a preferably regular electrode lattice structure comprising a plurality of multipole elementary cells that lie side-by-side and that comprise at least three single electrodes respectively. Each internal electrode of the lattice belongs to a plurality of multipole elementary cells.

In another design of the invention, the individual electrodes form, for example, a regular triangular lattice, in which every three adjacent single electrodes may be coupled to form a tripole; or a regular rectangular lattice, in which every four adjacent single electrodes may be coupled to form a quadrupole. The generated stimulation fields of every two adjacent multipoles may exhibit components that rotate simultaneously counter-clockwise.

The design of the inventive measures to apply phase-shifted alternating voltage signals to the individual electrodes of a multipole elementary cell takes into consideration an image information component and a signal shape component as additional factors that can be chosen on an individual basis for the individual electrodes. The image information component includes the image information to be perceived; and the signal shape component includes additional signal conditioning measures, such as a pulsed drive with predefined pulse parameters.

In an especially advantageous embodiment, the invention provides a retina implantable micro-electrode array, in which all of the individual electrodes are disposed on one side of a carrier chip and are actuated in a coupled manner in one of the aforementioned ways as tripoles or higher multipoles, so that a multipole stimulation field with rotating field contributions of the individual multipoles for stimulating the retina is produced. At the same time the field contributions of the adjacent multipoles may rotate simultaneously and counter-clockwise.

Advantageous embodiments of the invention are depicted in the drawings and are described below.

DETAILED DESCRIPTION OF THE DRAWINGS

Figure 1:
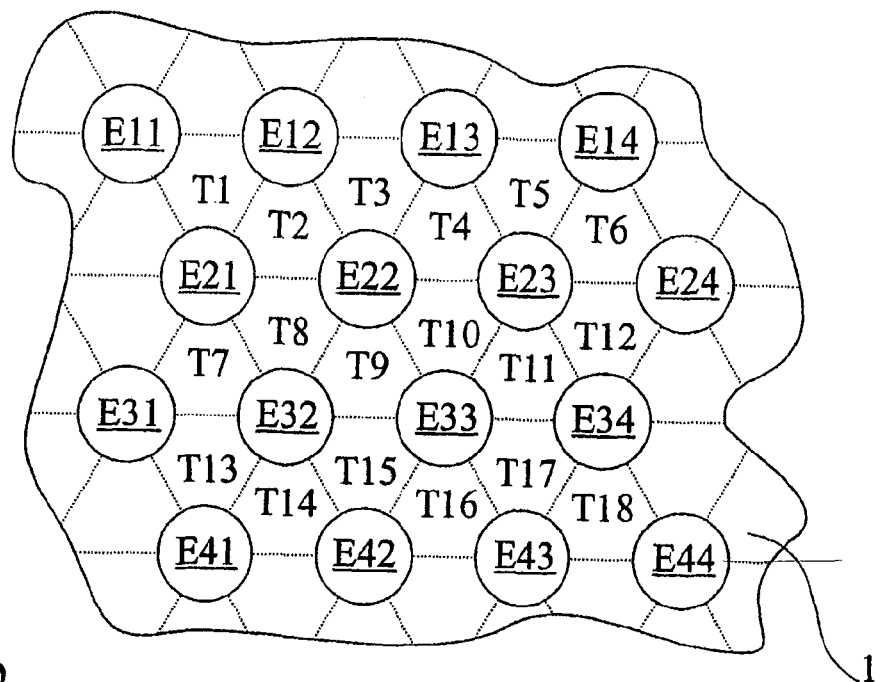
FIG. 1 is a schematic top view of a detail of a multi-electrode array, which can be used, for example, for a retina implant and which exhibits a triangular lattice structure of the individual electrodes.

FIG. 1 is a schematic top view of a detail of a micro/multi-electrode array 1, which exhibits a number n-m of individual electrodes Eij, where i=1, 2, . . . , n and j=1, 2, . . . , m. The individual electrodes are arranged in a regular triangular lattice structure, as symbolized by the triangular lattice lines between the electrodes Eij. In this respect n and m are arbitrary, preferably relatively large natural numbers, for example, between 10 and 1,000. Unless stated otherwise below, the electrode array 1 is, moreover, of any one of the conventional implantable types in active contact with a biological material that can be electrically stimulated. In particular, it can be realized as a retina implant chip for subretinal or epiretinal implantation.

The electrode triangular lattice includes all of the necessary electrodes, i.e., the stimulation electrodes and the counter-electrodes, where each electrode Eij acts as a stimulation electrode and a counter-electrode. In particular, every three adjacent electrodes are gathered together to form a tripole elementary cell. That is, they are driven in a coupled manner as a tripole—or example, the electrodes E11, E12 and E21 as a first tripole T1; the electrodes E12, E22 and E21 as a second tripole T2, etc., where the tripole designations T1, T2, . . . are entered into the respective center of the triangle. Since every point in the triangular lattice has six adjacent neighbors, each individual electrode Eij has six tripoles. At the same time a tripole T1, T2, . . . can be defined as an image point or rather a pixel, e.g., of a retina implant.

Figure 2:
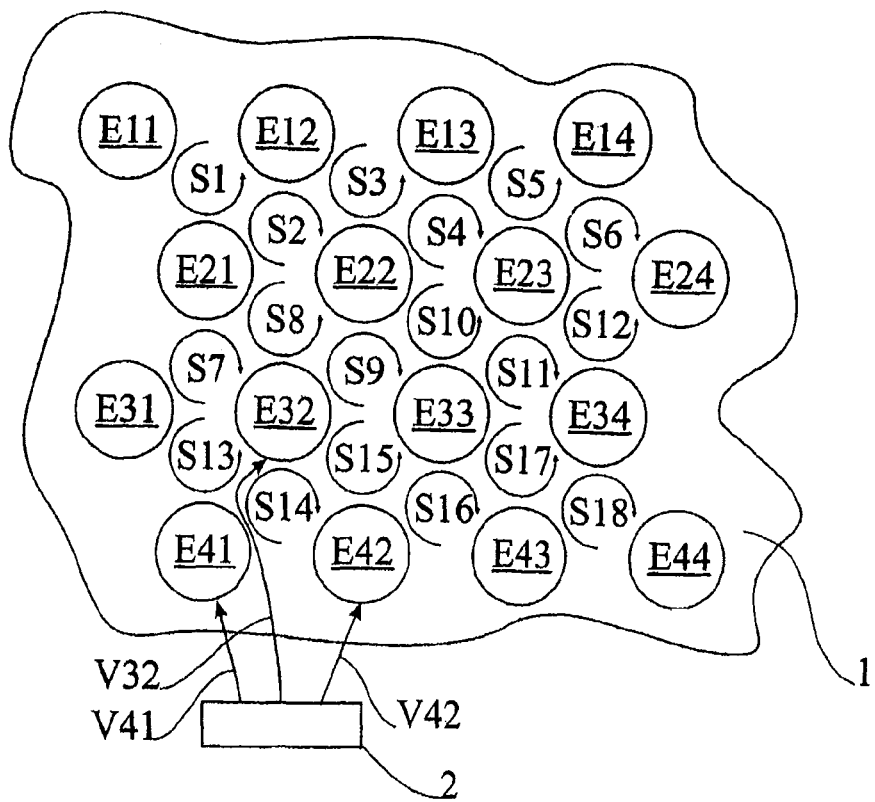
FIG. 2 is a top view of the configuration of FIG. 1 in a tripole drive mode with counter-clockwise rotating tripole stimulation current vectors.
Figure 3A:
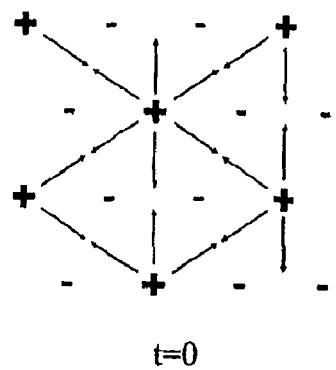
FIGS. 3A to 3F are diagrams of moments depicting the amplitude and polarity of the alternating drive voltages and the drive field vector directions for the drive mode, according to FIG. 2, at a number of different times of an alternating voltage period.
Figure 3B:
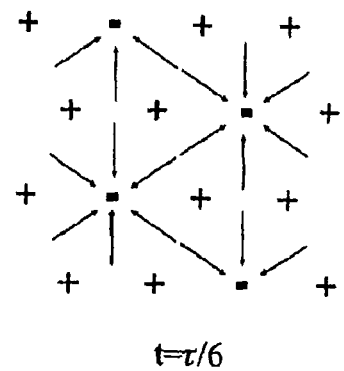
Figure 3C:
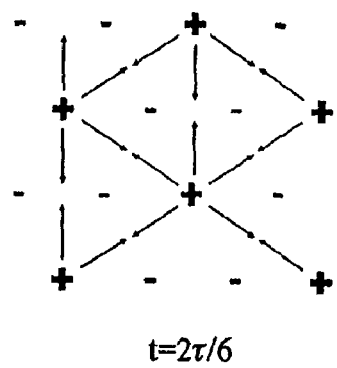
Figure 3D:
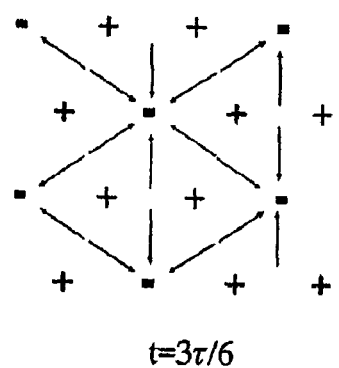
Figure 3E:
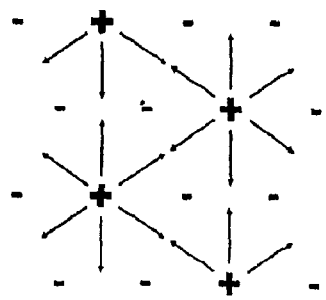
Figure 3F:
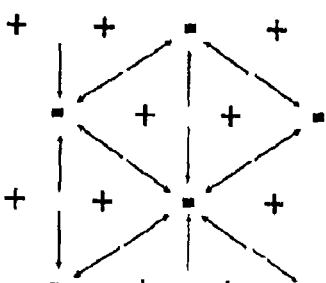
Figure 4:
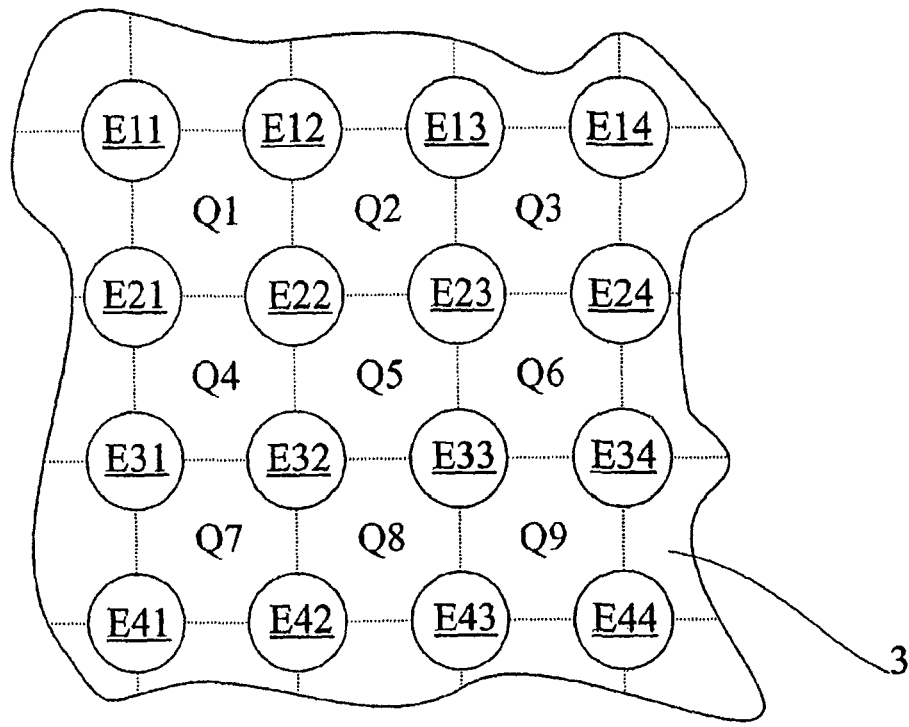
FIG. 4 is a view, according to FIG. 1, for a multi-electrode array with a rectangular lattice structure for the individual electrodes.

A suitably coupled drive of the individual electrodes Eij with phase-shifted alternating voltage signals makes it possible to produce with the triangular lattice a collective stimulation current field with field contributions S1, S2, . . . of the individual tripoles T1, T2, . . . . The individual tripole current fields S1, S2, . . . exhibit, as indicated in FIG. 2, a rotation component about a respective tripole axis and, thus, about an axis, which is parallel to the local normal direction of the electrode array 1 and which is the strongest in the center of the respective tripole T1, T2, . . . and decreases in the direction of the tripole electrodes. At the same time they exhibit an oscillation component, which is the strongest over the tripole electrodes and decreases in the direction of the center of the tripole. In order to bring about such a drive mode, the individual electrodes Eij are driven individually with a time-dependent drive voltage Vij(t) of the form $$Vij(t)=Iij(t)\cdot Bij(t)\cdot \sin(\omega t+Mij)$$

where Iij(t) denotes a time-dependent image matrix; Bij(t) denotes a time-dependent signal shape matrix; and Mij denotes a phase matrix, which can be chosen in the present example of a tripole configuration as follows:

$Mij=(2\pi/3)\cdot Sij+\pi/2$, with the following matrix $Sij$:

$$Sij = \begin{matrix} 0 & 1 & 2 & 0 & . \\ 2 & 0 & 1 & 2 & . \\ 0 & 1 & 2 & 0 & . \\ 2 & 0 & 1 & 2 & . \\ . & . & . & . & . \end{matrix}$$

Consequently the phase matrix Mij indicates the phase shift of the drive voltage signal Vij between the individual electrodes Eij. Clearly the phase of the drive voltage Vij alternates on account of the phase matrix Mij between every two electrodes of a respective tripole T1, T2, . . . by $2\pi/3$ (modulo $\pi$), as in the case of a conventional three-phase alternating voltage of a three-phase current supply system.

In addition, the time-dependency of the drive signal Vij(t) for each individual electrode Eij can be influenced in a multiplicative manner, according to the above equation, by means of the image matrix Iij(t) and the signal shape matrix Bij(t), as is generally known for driving stimulation electrodes in retina implants, to which reference may be made. In particular, the image matrix Iij represents the space-resolved image information that is to be perceived, as it is delivered, for example, by an electronic imaging unit, which can also be, in particular, a photodiode arrangement of a type that is customary for retina implants. The signal shape matrix Bij (also called by its English expression "beat matrix") is used to adjust a signal shape, which is suitable for the respective application, for the drive signals Vij, for example, a pulsed signal with predefinable pulse parameters, like the pulse amplitude and the pulse duration. In this case the voltage pulse is chosen with a preferably shorter duration than the tripole rotation period $\tau=(2\pi/\omega)$.

In the concrete case suitable signal shapes (for example, such shapes that have been tried and tested by experiment or are deemed to be suitable for other reasons) are chosen by a suitable choice of the signal shape matrix with the elements Bij(t). They include short-term pulses of less than one millisecond duration, e.g., in the shape of a rectangle. The result of reproducing such short-term pulses with Bij(t), in conjunction with a rotation period $\tau=(2\pi/\omega)$ of e.g., in the magnitude of 20 milliseconds, is that the stimulation signal during rotation occurs only in a narrow angular range, which can be called the "shot direction". There are then basically two possibilities. In the first possibility the shot direction changes with the repeated sending of the stimulation signal. This possibility can be used, for example, if a relatively conservative stimulation (that is, low values of the voltages applied to the electrodes) is desired, but at which neural cells are still "hit" (that is, are stimulated). In the second possibility, the shot direction does not change with repeated sending of the stimulation signal for each individual multipole. It changes only in a predefined manner upon transfer to other multipoles of the array. This second possibility can be used, if there are neural cells or parts thereof that are not to be stimulated or are to be stimulated only with lower probability. In the case of epiretinal application, they include, for example, the continuous axons, which conduct the information from more remote areas of the field of vision to the optic nerve. In this way the additional degree of freedom, which is gained by the field rotation in connection with the signal shape, is used to shape the stimulation signals.

As a result, the drive signal Vij of the above-described type for the individual electrodes Eij leads to a stimulation current field, which is made up of the individual tripole stimulation current fields of the tripoles T1, T2, . . . , which are modulated with the image information Iij and the signal shape Bij, which is pulsed in the usual way. In order to provide the individual drive signals Vij for the individual electrodes Eij, any well-known means for this purpose may be used; FIG. 2 shows such means only schematically as a drive voltage supply unit 2. As a substitute for the drive of all individual electrodes Eij, only the supply unit for the three electrodes E32, E41 and E42 of the tripole T14 is shown explicitly in FIG. 2. The unit 2 can be located in its entirety or partially on the array chip 1; and, depending on its application, can be of the passive or active type (that is, can be fed solely by the incoming visible light or the additionally supplied external energy). The unit 2 can include, in particular, standard photodiode elements (not illustrated in detail) for the space-resolved acquisition of the image information to be perceived.

FIG. 2 illustrates the simplified case of viewing a "white wall"—that is, Iij(t)=1 for all i and j and constant over the viewed time t, and without signal conditioning—that is, Bij (t)=1 for all i, j and t. As one can infer directly from the above equations, the result is then a pure tripole voltage drive of the electrodes Eij.

In the schematic top view of FIG. 2 (that is, in the projection on the electrode array plane), the individual tripole stimulation current fields S1, S2, . . . exhibit a component, which rotates about the respective tripole axis at the angular speed $\omega$ of the drive alternating voltage Vij (that is, about an axis orthogonal locally to the electrode array 1). This rotation component is the strongest in or rather over the center of the tripole, where the field lines exhibit a horizontal tangent (that is, a tangent which is parallel to the electrode array plane), and decreases in the direction of the three participating electrodes, a state that is well-known for a tripole alternating field. The rotation components of the respective second to the next tripoles rotate clockwise or counter-clockwise. That is, the rotation components of the respectively adjacent tripoles rotate counter-clockwise. At the same time the tripole current fields (a state that is not explicitly illustrated here for the sake of simplicity) exhibit an oscillation component, which is the strongest at or rather over the electrodes and decreases in the direction of the center of the tripole.

One must also make sure that owing to the charging/discharging characteristic of the electrodes there is usually a time phase difference between the rotation of the actuated voltage field and the rotation of the stimulation current field. In the linearized approximation for the charging/discharging characteristic (that is, the capacitor approximation), this phase difference can be calculated analytically, as generally well-known. Furthermore, one must make sure that the said currents apply to an electrically homogeneous biological material, which is accepted as the model.

Even if the above scenario represents only a qualitative estimate of an idealized case, it still follows for the general concrete case that upon determining a suitable drive voltage Vij(t) preferably by means of a computer unit, for example, as a part of the drive voltage supply unit 2, the stimulation current vectors S1, S2, . . . in each tripole area T1, T2, . . . of the electrode triangular lattice exhibit a rotation component about the tripole axis with a counter-clockwise rotation direction of the stimulation current vectors of the adjacent tripoles and an oscillation component that is superimposed for this purpose.

The rotation component realizes a "lighthouse effect" of the stimulation current field. That is, in each tripole area T1, T2, . . . there are rotating stimulation current vectors S1, S2, . . . , as illustrated schematically in the projection on the electrode array plane in FIG. 2. These stimulation current vectors S1, S2, . . . , which rotate at the fundamental frequency c) of the electrode-driving alternating voltage Vij(t), scan time-dependent a certain stimulation volume with a number of different vector direction.

FIGS. 3A to 3F illustrate in a self-explanatory way the details of how the rotating stimulation vector component is produced by this special tripole-alternating voltage drive of the electrodes. For the sake of simplifying this drawing, the elements of the image matrix Iij and the signal shape matrix Bij are set equal to 1. In addition, for each triangular lattice point in FIG. 2 (that is, for each electrode Eij) the polarity "+" or "−" of the voltage that is available at that instant is shown at intervals $\Delta t = \tau/6$ of a sixth of the period $\tau = 2\pi/\omega$ of the driving alternating voltage in a diagram of the respective moments. The higher amplitude is shown with thicker polarity signs. In addition, the momentary horizontal vector components of the applied electric field are indicated qualitatively as arrows, which occur in the center of each tripole area for the respective point in time. The chronological sequence of the diagrams of FIGS. 3A to 3F shows clearly that and how the component of the applied field in the central area of each tripole area rotates at the frequency of the driving alternating voltage, said component being parallel to the array surface. In the concrete case the time-dependent influence is also superimposed by means of the image matrix Iij(t) and the signal shape matrix Bij(t).

The availability of a rotating stimulation current field means now especially in the application as a retina implant a significant increase in the probability that inside a given retinal tissue volume a stimulation current vector will hit in its intensity and direction a cell of the retina in such a manner that its excitation threshold value is exceeded, so that a neural stimulation is triggered in it. Said neural stimulation can be passed on as space-resolved image information. At the same time it must be considered that the response sensitivity of the axons and the dendrites of the retinal tissue, which are typically of a cylindrical structure, varies as a function of the direction.

Consequently this increases the stimulation efficiency. In addition, the rotation of the stimulation current field increases the stimulation volume, since cells at a greater distance can still be hit with an adequate stimulation current, if said current has rotated into an advantageous direction. Another contributing factor is that, starting from the electrode array surface, a subgroup of the field lines of the tripole field—just like any other higher multipole field—moves away in a noticeable manner from the array surface with still relevant excitation current intensity and returns again in the manner of a curve to said array surface. In order to achieve a high stimulation efficiency and stimulation volume, the oscillation component of the stimulation current field makes its contribution in that it acts especially in the areas over the electrodes, whereas the rotation component acts especially in the area between the electrodes. The occurrence of a current intensity that is locally too high and that could lead to tissue damage is avoided.

Figure 5:
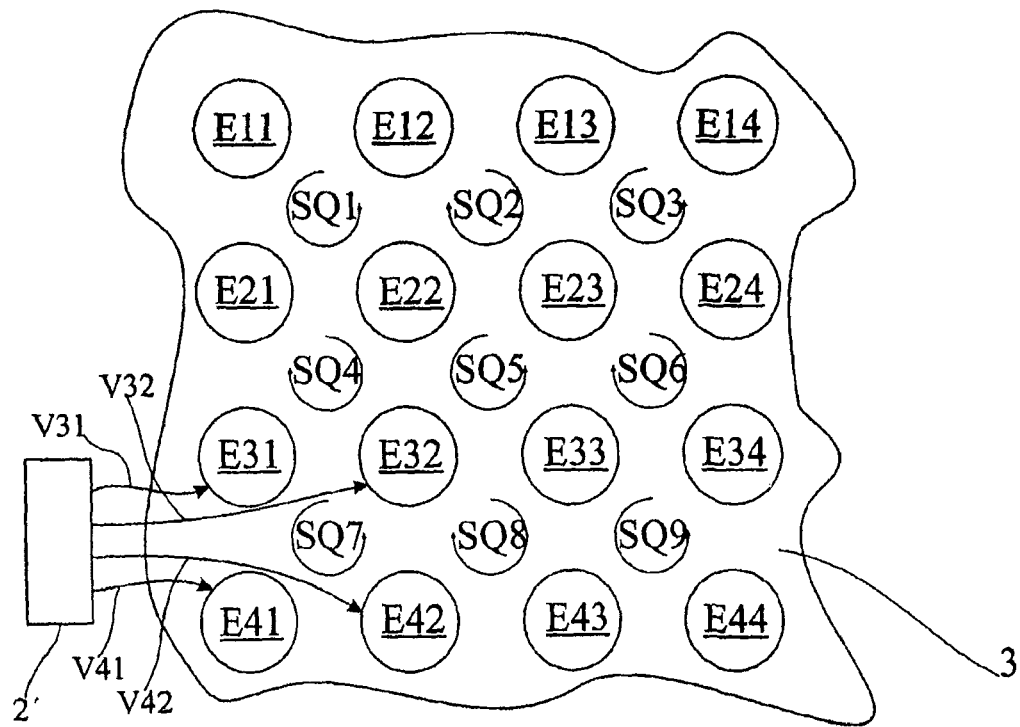
FIG. 5 is a view, according to FIG. 2, for a quadrupole drive mode of the electrode array of FIG. 4.
Figure 6A:
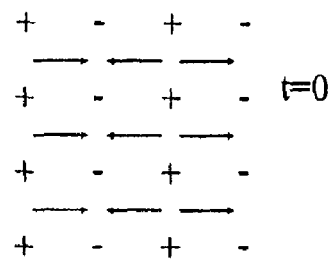
FIGS. 6A to 6H are diagrams of moments, according to FIGS. 3A to 3F, for the quadrupole drive mode, according to FIG. 5, at a number of different times of an alternating voltage period.
Figure 6B:
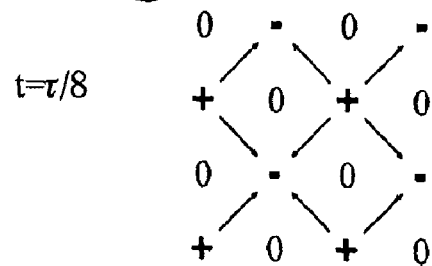
Figure 6C:
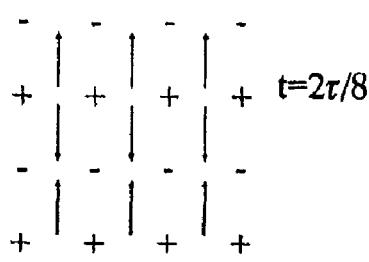
Figure 6D:
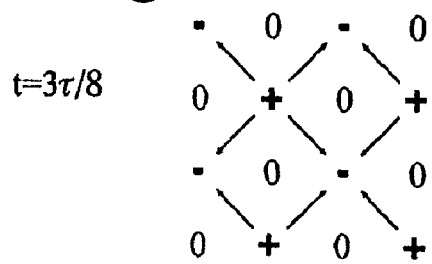
Figure 6E:
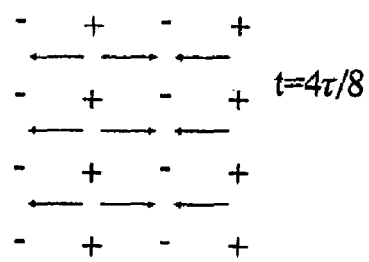
Figure 6F:
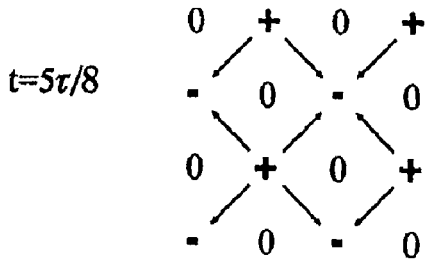
Figure 6G:
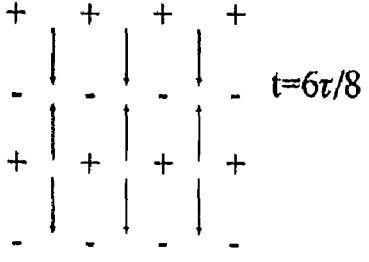
Figure 6H:
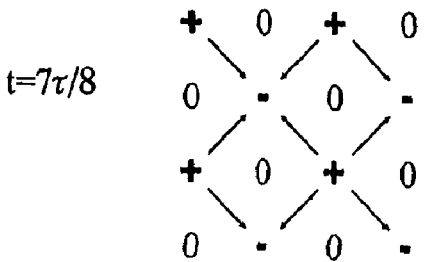

FIGS. 4, 5 and 6A to 6H illustrate, as another embodiment of the invention, a micro/multi-electrode array 3, which can be used in turn especially as a retina implant. This embodiment is analogous to the above-described tripolar electrode array, but here the individual electrodes Eij are arranged in a regular rectangular lattice, where it may be, in particular, a square lattice, with a number n of lines and a number m of columns, i.e., i=1, . . . n and j=1, . . . m. Every four adjacent electrodes form a quadrupole elementary cell Q1, Q2, . . . , in that they are driven correspondingly. Since in the rectangular lattice every internal electrode has four adjacent neighbors, it is a member of four adjacent quadrupoles. Unless stated otherwise below, this quadrupolar multi-electrode array matches in its functionality and its properties and advantages the above-described tripolar multi-electrode array, to which reference is made. At the same time FIG. 4 corresponds to FIG. 1; FIG. 5, to FIG. 2; and FIGS. 6A to 6H correspond to FIGS. 3A to 3F.

Especially in stimulation mode the individual electrodes Eij of the rectangular electrode lattice can be driven in turn with a driving alternating voltage Vij(t) of the form $$Vij(t)=Iij(t) \cdot Bij(t) \cdot \sin(\omega t + Mij),$$

where the image matrix Iij, the signal shape matrix Bij and the phase matrix Mij have the same meaning, as explained above with respect to the tripolar configuration. In analogy with the rectangular lattice, the phase matrix Mij is suitable, compared to the above tripolar example, to be modified for the purpose of quadrupole coupling of every four adjacent individual electrodes Eij. One possible choice for the phase matrix Mij is $$Mij=(\pi/2) \cdot Sij+(3\pi/4),$$

where for the quadrupole case the matrix Sij has the following form.

$$sij = \begin{matrix} 0 & 1 & 0 & 1 & 0 & 1 \\ -1 & 2 & -1 & 2 & -1 & 2 \\ 0 & 1 & 0 & 1 & 0 & 1 \\ -1 & 2 & -1 & 2 & -1 & 2 \\ 0 & 1 & 0 & 1 & 0 & 1 \\ -1 & 2 & -1 & 2 & -1 & 2 \\ . & . & . & . & . & . \end{matrix}$$

Every quadrupole Q1, Q2, . . . may be defined in turn as an image point or rather a pixel of a retina implant. Apart from the modulation, which is explained above with respect to the tripolar example, by means of the time-dependent image matrix Iij(t), which contains the image information to be perceived, and by means of the time-dependent signal shape matrix Bij(t), which determines preferably the production of short-term pulses, one can infer from the above equations the said quadrupole drive of the individual electrodes Eij. This drive in turn can be brought about by a drive voltage supply unit 2', which is designed to match. This is indicated in FIG. 5, acting as a substitute, by means of the drive of the four electrodes E31, E32, E41 and E42 for the quadrupole Q7. As shown in the schematic drawing in FIG. 5, a quadrupolar stimulation current field SQ1, SQ2, . . . with a rotation component is produced in the respective quadrupole area Q1, Q2, . . . . That is, the stimulation current field lines of each quadrupole Q1, Q2, . . . rotate in the central area of the quadrupole about the quadrupole axis, which runs parallel to the local normal direction of the electrode array 3, at the angular speed ω of the excitation voltage Vij. At the same time the rotation components of the adjacent quadrupoles rotate in turn counter-clockwise. Consequently the result even for this embodiment is the desired "lighthouse effect" of the rotating stimulation current vectors, here for the case of the local quadrupole fields.

FIGS. 6A to 6H show this feature with even more detail in the essentially self-explanatory diagrams of moments. In accordance with the FIGS. 3A to 3F in the above tripolar example, the polarity and the intensity of the momentary drive voltage Vij are shown at the respective lattice point (that is, the respective individual electrode Eij) and the resulting electric field vectors in the center of each quadrupole at equidistant time intervals of a period τ=2π/ω; here at time intervals of Δt=τ/8. The sequence of schematic snapshots shows in turn very clearly that the component (which runs parallel to the array plane) of the applied electric field in the center of each quadrupole field Q1, Q2, . . . rotates at the angular speed ω of the drive voltage Vij; and the drive voltage Vij for the different electrodes Eij is chosen in such a manner that the drive voltage signal Vij for each electrode Eij contributes in a phase correct manner to each of the four multipoles, to which each internal electrode belongs. This results in a stimulation current total field, to which all quadrupoles Q1, Q2, . . . contribute in a constructive manner in the form of the individual quadrupole current fields SQ1, SQ2, . . . with a rotation component, with the said counter-clockwise rotation of the respective adjacent quadrupole current fields SQ1, SQ2, . . . It must be stated for the sake of completeness that even in this example the rotation component in the quadrupole center is the most pronounced and decreases in the direction of each of the four participating electrodes. At the same time an oscillation component is superposed on the rotation component. Said oscillation component is inversely the most pronounced over the electrodes and decreases in the direction of the center of the quadrupole.

Even though the drawings in FIG. 6A to 6H relate in turn to the simplified case of a "white wall" and Bij(t)=1 for all i, j and t, as explained above with respect to the tripolar case, this result is also qualitatively correct for the general case. In other words, in practice it is also possible to produce with the described quadrupole drive of the electrodes Eij by means of the corresponding drive means 2 of the rectangular electrode lattice multipole stimulation currents, here especially quadrupole stimulation currents, with self-superimposing rotation and oscillation components in the adjacent biological material, when the electrode array 3 is implanted in the active area of the biological material, for example, as a subretinal or epiretinal optical aid implant. The quadrupole configuration also has the advantages that were described above with respect to the tripole configuration and that entail an increase in the stimulation volume and the stimulation efficiency and the avoidance of locally too high currents or voltage drops. Thus, it is possible especially in the case of the quadrupole configuration, as explained above with respect to the tripole configuration, to either vary or fix the "shot direction" of the short-term pulses, which can be determined with the signal shape matrix Bij(t) and to use, thus, the additional degree of freedom of rotation for an optimal design of the stimulation signal.

As the above-described tripolar and quadrupolar embodiments clearly show, the invention provides a device for electrically stimulating biological material with high stimulation efficiency and large stimulation volume, to which end the rotation effect of the tripolar or higher multipolar stimulation currents and also their oscillation effect make crucial contributions. In addition, a high resolution capability can also be achieved if a plurality of individual micro-electrodes are arranged in a multi-electrode array. Owing to the special tripolar or higher multipolar, collectively interacting drive of the individual electrodes, problems associated with the monopolar and bipolar arrangements are largely avoided. In particular, there are no disturbing collective stimulation current effects, such as excessively high voltage drops, etc. even in the case of relatively high image brightness up to the case of a "white wall" and high electrode integration density.

As the above-described embodiments clearly show, the invention makes it possible, in particular, to produce stimulation fields as a multipole array, in which the stimulation field contributions of the next adjacent multipoles can rotate simultaneously, but counter-clockwise. It is self-evident that in alternative embodiments stimulation fields with different patterns of rotating multipole fields can also be produced by modifying the drive of the individual electrodes. In particular, the invention also includes embodiments with a time-alternating or time-pulsed drive of multipole elementary cells, which are constructed from three or more adjacent individual electrodes, so that a stimulation field, in which the stimulation fields of adjacent multipole elementary cells rotate in the same direction, but displaced in time, can also be produced, as desired.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

The invention claimed is:

1. A device for electrically stimulating biological material, in particular retinal material, comprising:

an electrode array, configured to be implanted to contact the biological material, said electrode array having a two-dimensional arrangement of individual electrodes (Eij), which upon actuation with a stimulation signal (Vij) produce a stimulation field (S1, S2, . . .) for the biological material, and an apparatus for actuating the individual electrodes (Eij) with the stimulation signal, said apparatus for actuating the individual electrodes (Eij) being configured to actuate the individual electrodes (Eij) with alternating field stimulation signals (Vij) so that the electrode array forms at least two tripolar or higher multipolar multipole elementary cells (T1, T2, . . . ; $Q_1$, $Q_2$, . . .) from three or more adjacent individual electrodes respectively, whereby the stimulation field (S1, S2, . . .), produced by the multipole elementary cells for the biological material exhibits a rotation component, and at least one of the individual electrodes belongs to at least two multipole elementary cells.

2. The device of claim 1, wherein the stimulation field, produced by the respective multipole elementary cells for the biological material, exhibits a field component which rotates about a multipole axis.

3. The device of claim 1, wherein the alternating field stimulation signals for the individual electrodes of the multipole elementary cell include phase-shifted components of an alternating voltage signal.

4. The device of claim 3, wherein the alternating field stimulation signals include an additional multiplicative image information component and an additional multiplicative signal shape component.

5. The device of claim 4, wherein the multipole elementary cells are actuated by the electrode actuating apparatus so that with the alternating field stimulation signals the stimulation fields of the various multipole elementary cells exhibit simultaneously rotating field components with adjacent multipole elementary cells that rotate counter-clockwise.

6. The device of claim 1, wherein the individual electrodes are arranged in a regular lattice, which forms a plurality of multipole elementary cells, which lie side by side, each internal individual electrode of the lattice structure belonging to a plurality of multipole elementary cells.

7. The device of claim 6, wherein the individual electrodes are arranged in a regular triangular lattice or a regular rectangular lattice.

8. The device of claim 6, wherein the alternating field stimulation signals include an additional multiplicative image information component and an additional multiplicative signal shape component.

9. The device of claim 6, wherein the multipole elementary cells are actuated by the electrode actuating apparatus so that with the alternating field stimulation signals the stimulation fields of the various multipole elementary cells exhibit simultaneously rotating field components with adjacent multipole elementary cells that rotate counter-clockwise.

10. The device of claim 1, wherein said device is configured as a retina implant and the electrode array is a microelectrode array, configured to be implanted in the retina and wherein the individual electrodes are all arranged on one side of a carrier chip.

11. The device of claim 10, wherein the multipole elementary cells are actuated by the electrode actuating apparatus so that with the alternating field stimulation signals the stimulation fields of the various multipole elementary cells exhibit simultaneously rotating field components with adjacent multipole elementary cells that rotate counter-clockwise.

12. A device for electrically stimulating biological material, in particular retinal material, comprising:

an electrode array, configured to be implanted to contact the biological material, said electrode array having a two-dimensional arrangement of individual electrodes (Eij), which upon actuation with a stimulation signal (Vij) produce a stimulation field (S1, S2, . . .) for the biological material, and means for actuating the individual electrodes (Eij) with the stimulation signal, said means for actuating the individual electrodes (Eij) being configured to actuate the individual electrodes (Eij) with alternating field stimulation signals (Vij) so that the electrode array forms at least two tripolar or higher multipolar multipole elementary cells (T1, T2, . . . ; $Q_1$, $Q_2$, . . .) from three or more adjacent individual electrodes respectively, whereby the stimulation field (S1, S2, . . .), produced by the multipole elementary cells for the biological material exhibits a rotation component, and at least one of the individual electrodes belongs to at least two multipole elementary cells.

13. A method for electrically stimulating biological material, said method comprising the steps of:

actuating individual electrodes, which are provided in a two-dimensional electrode array that is in contact with a biological material, with a stimulation signal (Vij) to produce a stimulation field (S1, S2, . . .) for the biological material, wherein said stimulation signal includes with alternating field stimulation signals (Vij) so that the electrode array forms at least two tripolar or higher multipolar multipole elementary cells (T1, T2, . . . ; $Q_1$, $Q_2$, . . .) from three or more adjacent individual electrodes respectively, and wherein the stimulation field (S1, S2, . . .), produced by the multipole elementary cells for the biological material exhibits a rotation component, and at least one of the individual electrodes belongs to at least two multipole elementary cells.

14. The method of claim 13 wherein the stimulation field, produced by the respective multipole elementary cells for the biological material, exhibits a field component which rotates about a multipole axis.

15. The method of claim 13, wherein the alternating field stimulation signals for the individual electrodes of the multipole elementary cell include phase-shifted components of an alternating voltage signal.

16. The method of claim 15, wherein the alternating field stimulation signals include an additional multiplicative image information component and an additional multiplicative signal shape component.

17. The method of claim 16, wherein the multipole elementary cells are actuated by the electrode actuating apparatus so that with the alternating field stimulation signals the stimulation fields of the various multipole elementary cells exhibit simultaneously rotating field components with adjacent multipole elementary cells that rotate counter-clockwise.

18. The method of claim 13, wherein the individual electrodes are arranged in a regular lattice, which forms a plurality of multipole elementary cells, which lie side by side, each internal individual electrode of the lattice structure belonging to a plurality of multipole elementary cells.

19. The method of claim 18, wherein the individual electrodes are arranged in a regular triangular lattice or a regular rectangular lattice.

20. The method of claim 18, wherein the alternating field stimulation signals include an additional multiplicative image information component and an additional multiplicative signal shape component.

21. The method of claim 18, wherein the multipole elementary cells are actuated by the electrode actuating apparatus so that with the alternating field stimulation signals the stimulation fields of the various multipole elementary cells exhibit simultaneously rotating field components with adjacent multipole elementary cells that rotate counter-clockwise.

22. The method of claim 13, wherein said device is configured as a retina implant and the electrode array is a microelectrode array, configured to be implanted in the retina and wherein the individual electrodes are all arranged on one side of a carrier chip.

23. The method of claim 22, wherein the multipole elementary cells are actuated by the electrode actuating apparatus so that with the alternating field stimulation signals the stimulation fields of the various multipole elementary cells exhibit simultaneously rotating field components with adjacent multipole elementary cells that rotate counter-clockwise.

* * * * *